(12) United States Patent
Howat et al.

(10) Patent No.: US 7,575,591 B2
(45) Date of Patent: Aug. 18, 2009

(54) PROSTHESIS GRAFT WITH Z PLEATING

(75) Inventors: William L. Howat, Weston, FL (US);
Tara Schaneville, Tampa, FL (US)

(73) Assignee: Cordis Corporation, Miami Lakes, FL (US)

( * ) Notice: Subject to any disclaimer, the term of this patent is extended or adjusted under 35 U.S.C. 154(b) by 305 days.

(21) Appl. No.: 10/725,147

(22) Filed: Dec. 1, 2003

(65) Prior Publication Data

US 2005/0119730 A1 Jun. 2, 2005

(51) Int. Cl.
*A61F 2/06* (2006.01)

(52) U.S. Cl. .............. 623/1.13; 623/1.28; 623/1.29

(58) Field of Classification Search ............. 623/1.28, 623/1.13, 1.29
See application file for complete search history.

(56) References Cited

U.S. PATENT DOCUMENTS

| | | | |
|---|---|---|---|
| 4,780,344 A | * | 10/1988 | Hoberman .......... 428/12 |
| 5,234,727 A | * | 8/1993 | Hoberman .......... 428/12 |
| 7,060,092 B2 | * | 6/2006 | Kuribayashi et al. ....... 623/1.29 |
| 2002/0091439 A1 | | 7/2002 | Baker et al. |
| 2004/0019375 A1 | * | 1/2004 | Casey et al. ......... 623/1.28 |

FOREIGN PATENT DOCUMENTS

| | | |
|---|---|---|
| CA | 2498162 | 4/2003 |
| EP | 0 666 006 A | 8/1995 |
| EP | 0 955 019 A | 11/1999 |
| FR | 2 334 488 A | 7/1977 |
| WO | WO 0278572 A1 * | 10/2002 |

* cited by examiner

*Primary Examiner*—Thomas J Sweet

(57) ABSTRACT

A prosthesis configured for establishing a fluid flow path through an artery or the like includes a generally cylindrical body portion formed from graft material. In accordance with a preferred aspect of the device, at least a portion of the graft material is profiled where the profile defines a geometric pattern, e.g. a series of Z pleats.

7 Claims, 6 Drawing Sheets

PROSTHESIS GRAFT WITH Z PLEATING

BACKGROUND OF THE INVENTION

1. Field of the Invention

The present invention relates to endovascular devices and, more particularly, to methods and apparatus for providing radial support thereto.

2. Description of Related Art

Over the past five years, there has been a great deal of research directed at developing less invasive, percutaneous, e.g., catheter directed, techniques for various medical treatments. This has been facilitated by the development of vascular stents, which can and have been used in conjunction with standard or thin-wall graft material in order to create a stent-graft or endograft. The potential advantages of less invasive treatments have included reduced surgical morbidity and mortality along with shorter hospital and intensive care unit stays.

While the percutaneous placement of endografts represent a significant improvement over conventional surgical techniques, there is a need to improve the endoprostheses, their method of use, and their applicability to varied biological conditions.

A need also exists to improve over current fabrication methods as they relate to ease of use and speed of assembly, to eliminate or reduce corrosion caused by metallic stents, to provide sufficient radial support in combination with prosthesis flexibility while reducing the potential for kinking, and to provide a prosthesis having a graft that is easily crimped and placed into a delivery system.

SUMMARY OF THE INVENTION

The prosthesis of the present invention overcomes the limitations briefly described above.

The present invention is directed to a means and method for providing support to a graft to maintain lumen patency by utilizing pleats formed and applied in a "Z" or similar pattern, to the graft material. This would replace part of the currently used metal substrate or scaffold structure used in the fabrication of covered stents, stent-grafts, endologs or other devices that require a substrate or scaffold to provide radial support to a covering. The pleats may be formed in the designated section of the graft material using a device similar to devices currently utilized.

The present invention is simple and inexpensive to manufacture. The sections supported by the "Z" pleats would preferably be non-metallic, thereby limiting any potential corrosion issues. The "Z" pleats would provide radial support and allow for increased flexibility reducing the potential of kinking. The "Z" pleats would also allow for the graft to be easily crimped and placed into a delivery system.

In accordance with an aspect of the invention, a prosthesis for maintaining lumen patency comprises a substantially cylindrical hollow body having a distal end and a proximal end, the body being formed from a self-supporting non-metallic graft material where at least a portion of the graft material includes a plurality of pleats disposed in a Z pattern to provide radial support and increased flexibility to the body.

In accordance with another aspect of the invention, a prosthesis for maintaining lumen patency comprises a hollow body portion having a distal end and a proximal end where the body is formed from a self-supporting non-metallic graft material. At least a portion of the graft material includes a plurality of pleats disposed in a geometric pattern that provides radial support to the body while maintaining flexibility.

The accompanying figures show illustrative embodiments of the invention from which these and other of the objectives, novel features and advantages will be readily apparent.

DESCRIPTION OF THE FIGURES

The foregoing and other aspects of the present invention will best be appreciated with reference to the detailed description of the invention in conjunction with the accompanying drawings. Throughout the figures and the description below, like numerals indicate the same element.

DETAILED DESCRIPTION OF THE INVENTION

The present invention may be used in any medical or therapeutic application in which a prosthesis is desirable or beneficial, including but not limited to the treatment of aneurysms such as aortic aneurysms.

The present invention is directed to a prosthesis configured for establishing a fluid flow path through an artery or the like and may be employed to maintain lumen patency. A prosthesis of the present invention includes a generally cylindrical body portion formed from graft material. In accordance with a preferred aspect of the invention, at least a portion of the graft material is profiled where the profile defines a geometric pattern.

Figure 1:
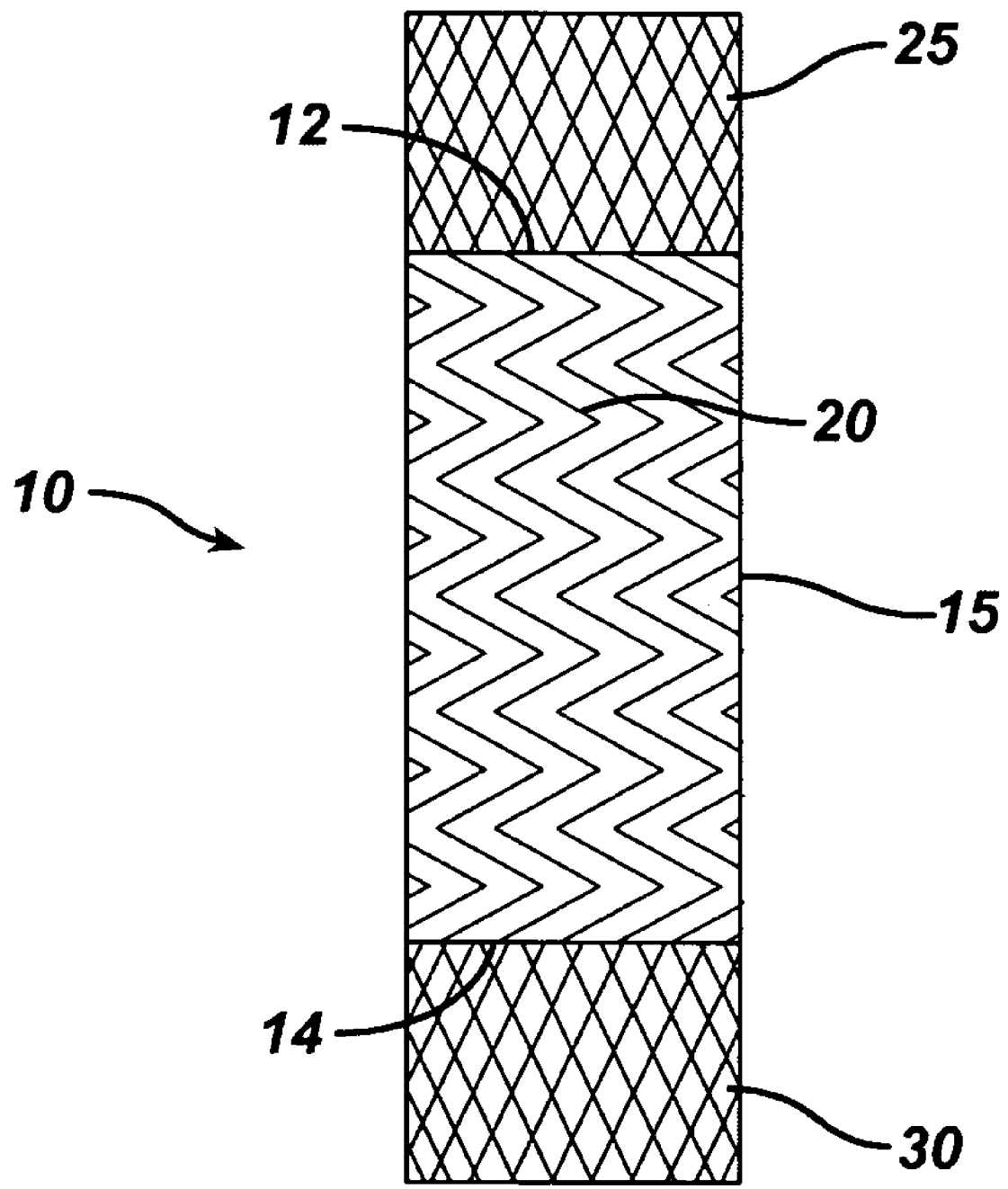
FIG. 1 shows a prosthesis in accordance with the present invention.

As illustrated in FIG. 1, prosthesis 10 includes a body portion 15 defining a fluid flow path formed from graft material. Body portion 15 includes an open proximal end 12 and an open distal end 14. In order to provide radial support to prosthesis 10 and to increase flexibility of prosthesis 10, at least a section of body portion 15 is provided with a profile comprising a geometric pattern 20.

In accordance with the invention, the profile of body portion 15 preferably comprises pleats but may also comprise corrugations or indentations. Geometrical pattern 20 and the graft material itself form a means for providing radial support for prosthesis 10, i.e., prosthesis 10 is self-supporting. In addition, geometrical pattern 20 and the graft material itself provide increased flexibility of prosthesis 10 and a reduction of kinking potential as compared to conventional prosthesis that employ graft material covering a metal support structure.

In keeping with the present invention, as illustrated in FIGS. 2-7, geometric pattern 20 preferably comprises a Z pattern, but may also include a sinusoidal pattern, an elliptical pattern, an oblique pattern, a helical pattern or any other pattern that provides radial support for prosthesis 10 while increasing flexibility.

The graft material of the present invention may be formed from various yarn materials or fibers including polyester, polypropylene, polyethylene or a combination of one or more of the foregoing. In terms of construction, the graft material may be one or more of the following constructions: woven, non-woven, knitted, braided or the like and may be of varying densities. For example, the graft material may include a woven region of a first density and a braided region of a second density.

Figure 2:
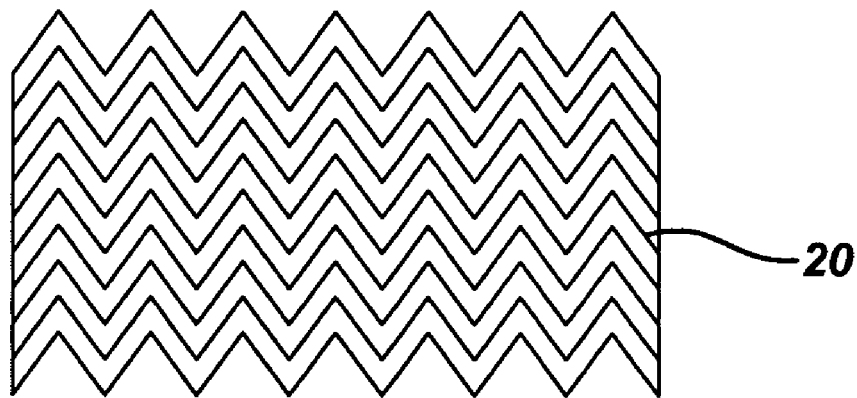
FIG. 2 illustrates a planar view a section of the graft material formed into a Z pattern.
Figure 3:
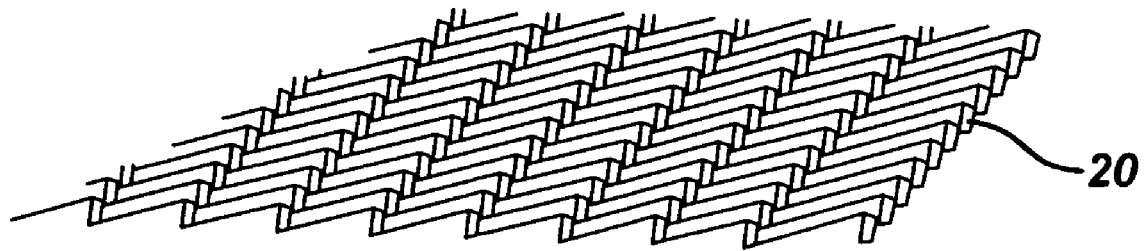
FIG. 3 depicts a perspective view a section of the graft material formed into a Z pleat pattern.
Figure 4:
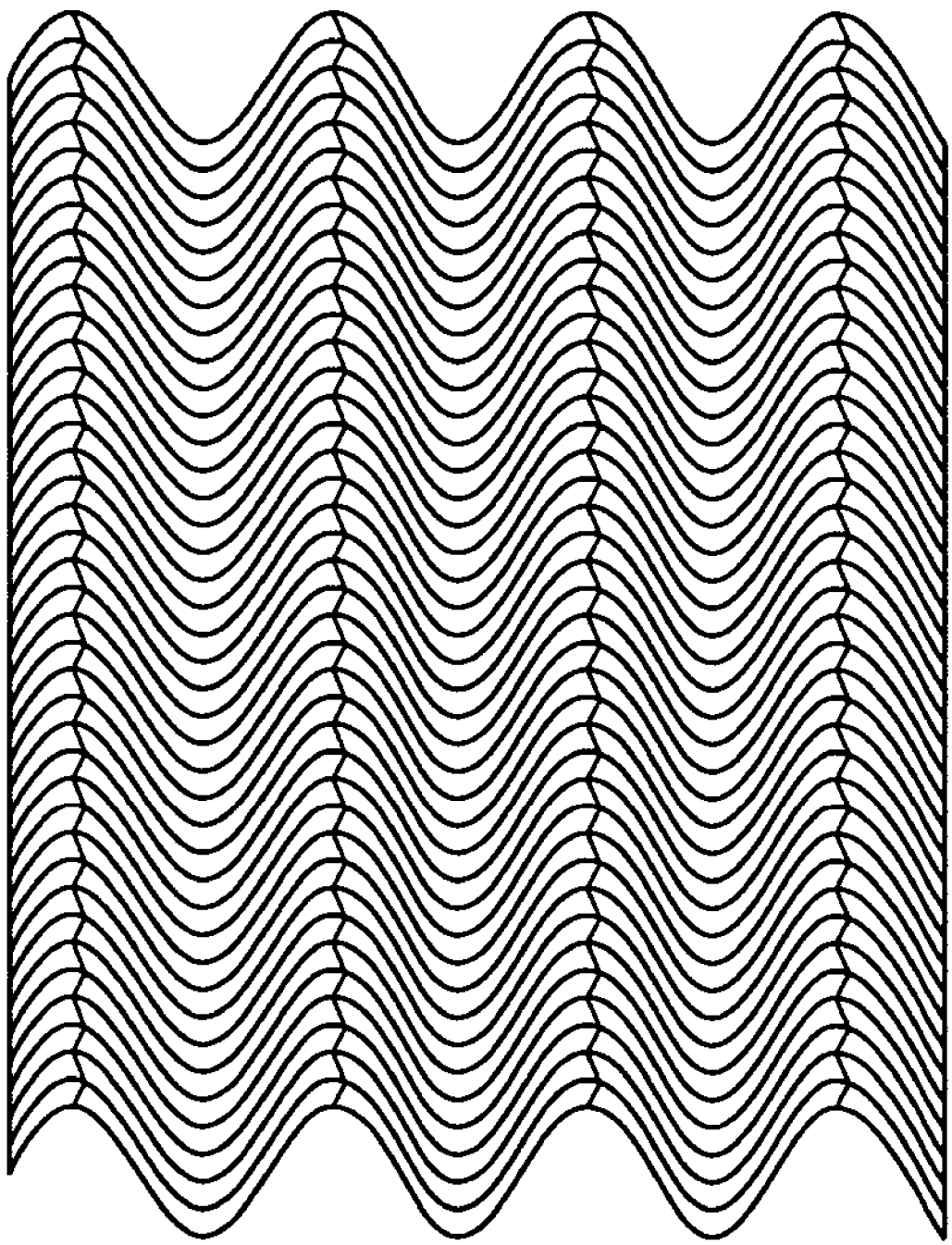
FIG. 4 is a plan view of a section of the graft material formed into a sinusoidal pattern.
Figure 5A:
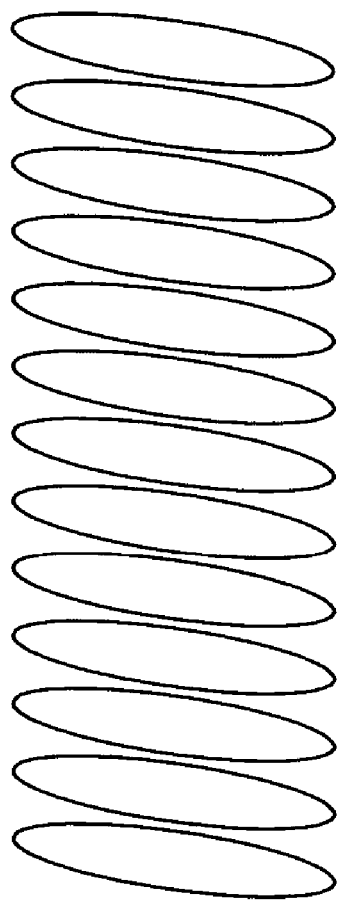
FIG. 5A is a schematic perspective view of a section of the graft material formed into an elliptical pattern.
Figure 5B:
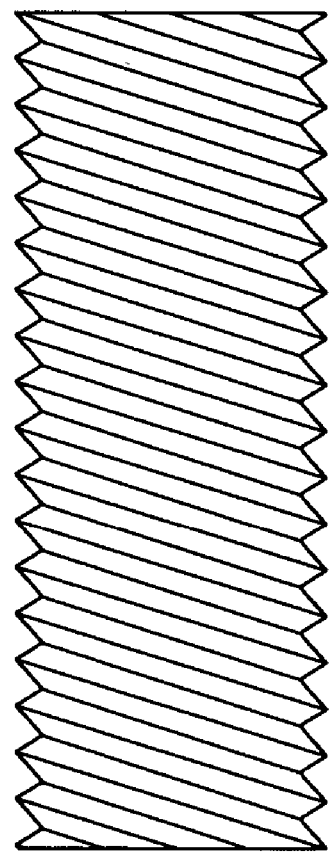
FIG. 5B is a side elevational view of a section of the graft material formed into an elliptical pattern.
Figure 6A:
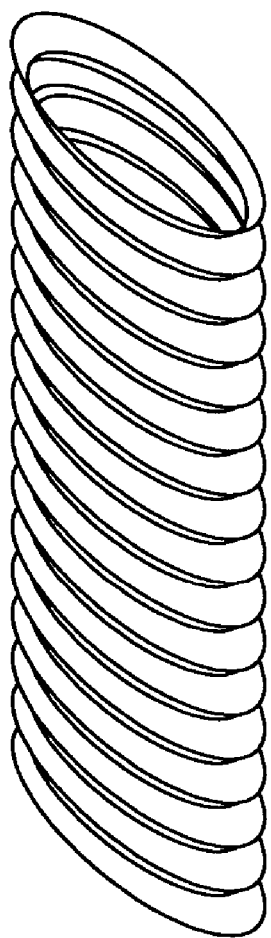
FIG. 6A is a schematic perspective view of a section of the graft material formed into an oblique pattern.
Figure 6B:
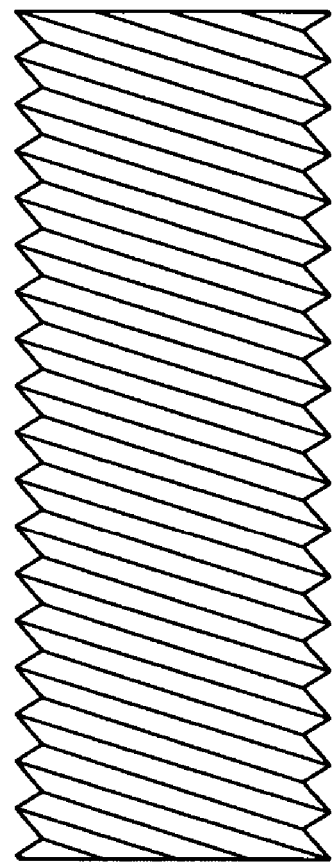
FIG. 6B is a side elevational view of a section of the graft material formed in an oblique pattern.
Figure 7A:
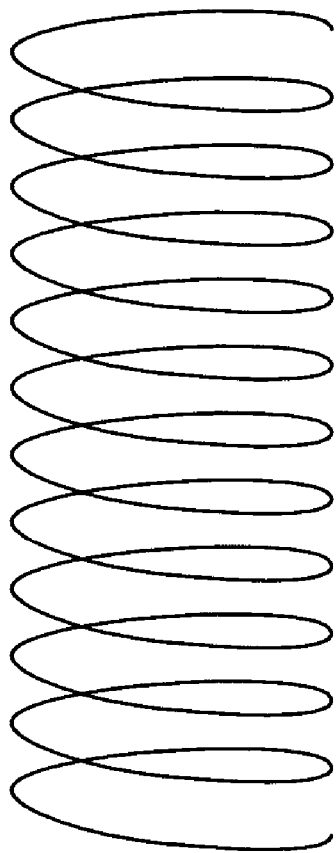
FIG. 7A is a schematic perspective view of a section of the graft material formed into a helical pattern.
Figure 7B:
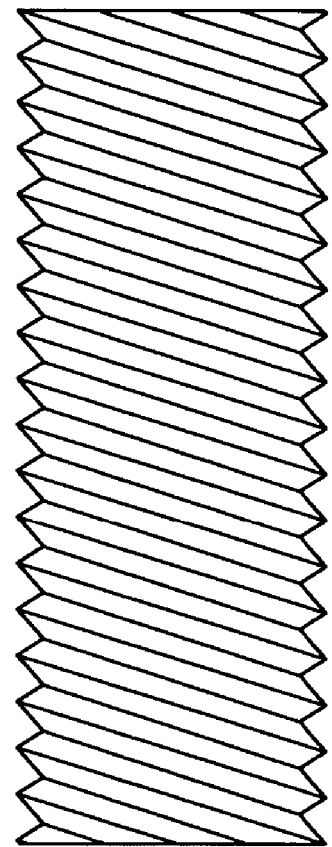
FIG. 7B is a side elevational view of a section of the graft material formed into a helical pattern.

As shown in FIGS. 2 and 3, geometric pattern 20 preferably includes a plurality of longitudinal Z pleats extending along its surface, generally parallel to the longitudinal axis of the prosthesis. The pleats allow the prosthesis to collapse around its center, much as it would be when it is delivered into a patient. The pleats come together as a series of regular folds that pack together efficiently. This provides a relatively low profile delivery system, and provides for a controlled arid consistent deployment therefrom. It is believed that this configuration minimizes wrinkling and other geometric irregularities to which prosthesis 10 may otherwise be prone. Upon subsequent expansion, the prosthesis assumes its natural cylindrical cross-sectional shape, and the pleats or folds uniformly and symmetrically open.

In addition, the Z pleats help facilitate prosthesis manufacture, in that they make prosthesis 10 easier to crimp and thus load onto a delivery system. The force required to push prosthesis 10 out of the delivery system may also be reduced, in that, in preferred embodiments, only the pleated edges of the graft make frictional contact with the inner surface of the delivery system. One further advantage of the pleats is that blood tends to coagulate generally uniformly in the troughs of the pleats, discouraging asymmetric or large clot formation on the graft surface, thereby reducing embolus risk.

In other exemplary embodiments of the invention, geometric pattern 20 may comprise pleats disposed longitudinally, axially, or combinations of both. Under typical conditions, these pleats will form a relatively consistent pattern, e.g., pleats all of a certain length. In the exemplary embodiments of the present invention for use in a highly angulated artery, it may be desirable to vary the pattern or patterns of pleats. For example, in the area of greatest angle, it may be desirable to provide a prosthesis having one or two (or more, as needed) pleat interruptions or axially pleated sections separated by a shorter longitudinally pleated section or sections. It is believed that increasing the number of axial pleats in the highly angulated section of the artery reduces stress on the prosthesis, and may promote a more fluid tight fit of the system. In accordance with an alternate aspect of the present invention, the graft material may be formed into other pleated configurations or patterns, including but not limited to sinusoidal, elliptical, oblique, helical, or combinations thereof, as illustrated FIGS. 4-7. It is believed that by incorporating a pattern or pleat configuration according to the present invention, the graft and stent promotes or maintains improved lumen patency as compared to conventional methods of covering a stent with graft material.

In accordance with still another exemplary embodiment of the invention, one or both proximal end 12 and distal end 14 may be connected to anchors 25 and 30. Anchors 25 and 30 preferably comprise a support or lattice structure suitable for anchoring prosthesis 10 in a lumen. Anchors 25 and 30 may comprise an expandable lattice or network of interconnected struts. In accordance with the present invention, the anchors 25 and 30 may be variously configured. For example, the anchors 25 and 30 may be configured with struts or the like that form repeating geometric shapes. One skilled in the art will readily recognize that anchors 25 and 30 may be configured or adapted to include certain features and/or to perform a certain function(s), and that alternative designs may be used to promote that feature or function. In an exemplary embodiment the struts of proximal anchors 25 and 30 are configured into a diamond shape.

Anchors 25 and 30 may be formed of a wide variety of materials, all of which are well known to those skilled in the art. Preferably, anchors 25 and 30 are formed of a metal or metal alloy such as Nitinol.

Anchors 25 and 30 are preferably attached to proximal and distal ends 12 and 14 such that there is minimal overlap between anchors 25 and 30 and body portion 15. Because body portion 15 is self-supporting, unlike conventional prosthesis employ support structures covered by graft material, there is no need to provide body portion 15 with additional support structure.

Anchors 25 and 30 may be attached to body portion 15 by any number of structures or methods known to those skilled in the art, including adhesives, such as polyurethane glue; a plurality of conventional sutures of polyvinylidene fluoride, polypropylene, Dacron®, or any other suitable material; ultrasonic welding; mechanical interference fit; staples, rivets, or the like. In preferred embodiments of the invention, the connector is a suture or staple, even more preferably, having a knotted or nub end. Further, a connector may be formed from a radiopaque material or a fluorescent material, each of which allow the connector to be used as a marker.

It is important to note that any number of configurations of pleats may be utilized, including sinusoidal, elliptical, oblique, helical and combinations thereof. In addition, various fabrics and fabric constructions may be utilized. The fabric construction include woven, non-woven, knitted, braided and combinations thereof.

Although shown and described is what is believed to be the most practical and preferred embodiments, it is apparent that departures from specific designs and methods described and shown will suggest themselves to those skilled in the art and may be used without departing from the spirit and scope of the invention. The present invention is not restricted to the particular constructions described and illustrated, but should be constructed to cohere with all modifications that may fall within the scope of the appended claims.

What is claimed is:

1. An implantable medical prosthesis for maintaining lumen patency comprising a substantially cylindrical hollow body having a distal end and a proximal end and defining a longitudinal axis therebetween, the body being formed from a self-supporting non-metallic graft material and at least a portion of the graft material having a profile comprising a geometric pattern including plurality of pleats, disposed in a Z pattern in at least one of a radial and longitudinal direction, configured to provide radial support in a tubular organ, the plurality of pleats being configured to come together as a series of regular folds, a distal anchor having a substantially diamond shaped lattice structure formed from a self-expanding metallic material and a proximal anchor having a substantially diamond shaped lattice structure formed from a self-expanding metallic material, the distal and proximal anchors being affixed via sutures to the ends of the hollow body and having minimal overlap with the hollow body.

2. The prosthesis of claim 1 wherein at least a section of the self-supporting non-metallic graft material is woven.

3. The prosthesis of claim 1 wherein at least a section of the self-supporting non-metallic graft material is non-woven.

4. The prosthesis of claim 1 wherein at least a section of the self-supporting non-metallic graft material is knitted.

5. The prosthesis of claim 1 wherein the self-supporting non-metallic graft material includes polyester.

6. The prosthesis of claim 1 wherein the self-supporting non-metallic graft material includes polypropylene.

7. The prosthesis of claim 1 wherein the self-supporting non-metallic graft material includes polypropylene.

* * * * *